US010788490B2

(12) United States Patent
Ashworth

(10) Patent No.: US 10,788,490 B2
(45) Date of Patent: Sep. 29, 2020

(54) DRIED CELLULOSE-TREATED TISSUE FOR IN-VITRO COMPLEMENT ACTIVATION ASSAYS AND DIAGNOSTIC KITS

(71) Applicant: St. Jude Medical, Cardiology Division, Inc., St. Paul, MN (US)

(72) Inventor: Paul E. Ashworth, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 101 days.

(21) Appl. No.: 15/906,021

(22) Filed: Feb. 27, 2018

(65) Prior Publication Data

US 2018/0246094 A1 Aug. 30, 2018

Related U.S. Application Data

(60) Provisional application No. 62/464,697, filed on Feb. 28, 2017.

(51) Int. Cl.
*G01N 33/564* (2006.01)
*G01N 1/30* (2006.01)
*A61K 35/12* (2015.01)

(52) U.S. Cl.
CPC ........... *G01N 33/564* (2013.01); *A61K 35/12* (2013.01); *G01N 1/30* (2013.01); *G01N 2001/305* (2013.01); *G01N 2333/4716* (2013.01)

(58) Field of Classification Search
CPC .............. G01N 33/564; G01N 1/30; G01N 2333/4716; G01N 2001/305; A61K 35/12
See application file for complete search history.

(56) References Cited

U.S. PATENT DOCUMENTS 4,300,243 A 11/1981 Baumgartner
6,534,004 B2 * 3/2003 Chen .................. A01N 1/00
422/40
8,007,992 B2 8/2011 Tian et al.

FOREIGN PATENT DOCUMENTS

WO 9958082 A2 11/1999
WO 2008089365 A2 7/2008
WO 2015031124 A1 3/2015
WO 2017189941 A1 11/2017

OTHER PUBLICATIONS

Tang & Pikal, Pharmaceutical Research, vol. 21, No. 2, Feb. 2004, p. 191-200.*
SP Scientific, 2010, Basic Principles of Freeze Drying, Author John Barley, downloaded from the SP Scientific website, 12 pages of PDF.*
Wang et al., Carbohydrate Polymers, 2015, vol. 115, p. 54-61.*
"Biological Evaluation of Medical Devices—Part 4: Selection of Tests for Interaction with Blood", British Standard, Apr. 2009.
Daniel B. Lyle et al, "Screening biomaterials for functional complement activation in serum", Journal of Biomedical Materials Research—Part A., vol. 92A, No. 1, pp. 205-213, Jan. 2010.
International Search Report for PCT/US2018019821, dated Jun. 6, 2018.

* cited by examiner

*Primary Examiner* — Kade Ariani
(74) *Attorney, Agent, or Firm* — Lerner, David, Littenberg, Krumholz & Mentlik, LLP

(57) ABSTRACT

Methods of preparing a solid reference material so as to elicit a positive control response when tested for in-vitro complement activation include providing biological tissue; treating the tissue with an aqueous cellulose solution for a time sufficient to allow fluid in the tissue to be replaced by the aqueous cellulose solution; drying the cellulose-treated tissue by a vacuum-drying process or a lyophilization process to form dried tissue; and storing the dried tissue in a dry, ambient environment. The tissue prepared by these methods and its use in an in-vitro complement assay and diagnostic kit are also described.

18 Claims, 4 Drawing Sheets

DRIED CELLULOSE-TREATED TISSUE FOR IN-VITRO COMPLEMENT ACTIVATION ASSAYS AND DIAGNOSTIC KITS

CROSS-REFERENCE TO RELATED APPLICATIONS

The present application claims the benefit of the filing date of U.S. Provisional Patent Application No. 62/464,697 filed Feb. 28, 2017, the disclosure of which is hereby incorporated herein by reference.

BACKGROUND OF THE INVENTION

The complement system within blood serum is a complex plasma-enzyme system which consists of many components and acts in various ways to prevent damage due to invading foreign microorganisms. Complement is a group of over thirty plasma and cell-bound proteins that can be activated via three different initiation pathways, i.e., the antibody-dependent "classical" pathway, the anti-body-independent "alternative" pathway, and the lectin pathway. Through activation and interaction with its respective receptors on various immune cells, the complement system is closely linked to the adaptive immune response including both antimicrobial and antiviral actions. Consequently, an acute or chronic activation of the complement system presents serious health effects. Adverse systemic effects include pulmonary dysfunction and hypoxemia. Local complement activation may result in chemoattraction of polymorph-nuclear cells and their activation, adherence, degranulation, and superoxide production.

Some blood-contacting biomaterials used in medical devices are known to activate the complement system. Cuprophan® (3M Company), a membrane made of cellulose with free hydroxyl groups, has been used for hemodialysis and is a typical example. Materials being considered for new medical and dental devices may need to be tested for complement activation. International Organization for Standardization (ISO) standard 10993-4 (Biological evaluation of medical devices Part 4: Selection of tests for interaction with blood) provides general guidelines and test requirements for evaluating medical and dental devices that are intended for use in contact with blood.

As categorized in ISO 10993-1 (Biological evaluation of medical devices Part 1: Evaluation and testing), the classification of medical and dental devices intended for use in contact with blood includes, but is not limited to, non-contact devices such as in-vitro diagnostic devices; external communicating devices that serve as an indirect blood path such as cannulae, extension sets, blood collection devices, devices for the storage and administration of blood and blood products (e.g., tubing, needles and bags) and cell savers; external communicating devices in contact with circulating blood such as atherectomy devices, blood monitors, catheters, guidewires, intravascular endoscopes, intravascular ultrasound, intravascular laser systems, retrograde coronary perfusion catheters, cardiopulmonary bypass circuitry, extracorporeal membrane oxygenators, hemodialysis/haemofiltration equipment, donor and therapeutic apheresis equipment, devices for the absorption of specific substances from blood, interventional cardiology and vascular devices and percutaneous circulatory support systems; and implant devices such as annuloplasty rings, mechanical or tissue heart valves, prosthetic or tissue vascular grafts, circulatory support devices (e.g., ventricular-assist devices, artificial hearts and intra-aortic balloon pumps), inferior vena cava filters, embolization devices, endovascular grafts, implantable defibrillators and cardioverters, stents, arteriovenous shunts, blood monitors, internal drug delivery catheters, pacemaker leads, intravascular membrane oxygenators (e.g., artificial lungs) and leukocyte-removal filters.

ISO 10993-4 requires complement activation tests for devices that have permanent or extended contact with blood (i.e., at least 24 hours). Such devices include, but are not limited to, blood storage and administration equipment, blood collection devices, extension sets, catheters in place for more than 24 hours (e.g., intravascular endoscopes, intravascular ultrasound, laser systems, and retrograde coronary perfusion catheters), devices for the absorption of specific substances from blood, donor and therapeutic apheresis equipment and cell separation systems, extracorporeal membrane oxygenator systems, hemodialysis/haemofiltration equipment, percutaneous circulatory support devices, leukocyte removal filters, total artificial hearts, ventricular-assist devices, endovascular grafts, and prosthetic (synthetic) vascular grafts and patches including arteriovenous shunts.

In-vitro complement activation Enzyme-Linked Immunosorbent Assay (ELISA) kits are available for the quantitative measurement of complement in human plasma and serum. Available testing methods include: immunoassays for complement activation "split products" such as C4d, Bb, C3a, C4a, C5a, and SC5b-9; immunohistochemical demonstration of adsorbed activated complement components such as C3b, C4b, and C5b-9; and functional depletion of complement activity such as C9, as C9 is consumed in the Membrane Attack Complex (MAC). C3a and SC5b-9 are the "split products" from complement activation. The C3a and SC5b-9 assays are used to detect the amount of C3a and SC5b-9, respectively, in human serum. If the material in question activates the complement system, C3a and SC5b-9 will be generated in the serum and the amount of C3a and SC5b-9 will be increased as indicated in the ELISA. C9 is the pore-forming subunit of the MAC and plays a key role in the innate and adaptive immune response by forming pores in the plasma membrane of target cells. C9 will be consumed if the complement cascade is activated by a material to form the MAC. The C9 assay is used to detect the amount of C9 in human serum. If the material in question activates the complement system and the MAC is formed, C9 will be consumed and the amount of C9 in the serum will be reduced as indicated in the ELISA. ISO 10993-4 also requires that testing include a well-characterized reference material. The reference materials used should include negative and positive controls. All materials tested should meet the quality control and quality assurance specifications of the manufacturer and test laboratory.

However, a reliable surface-based reference material as a positive control has not yet been identified. Cobra venom factor (CVF) is typically used as a positive control for complement activation testing. CVF is supplied in a liquid form, and therefore does not provide a solid reference material mediated complement response. Moreover, adverse effects such as an exacerbation of tissue injury and an increase in granulocytes sequestered in the lung by CVF have been reported, and one should be very cautious with the interpretation of the data from the experiments when CVF is used as a positive control. Various other materials such as high-density polyethylene (HDPE), glass beads, filter discs, polyurethane, and zymosan have been evaluated in complement activation assays, but do not provide satisfactory responses.

Therefore, there is a need to identify a solid reference material as a reliable positive control for in-vitro complement activation assays and diagnostic kits.

BRIEF SUMMARY OF THE INVENTION

The present invention relates to methods of preparing biological tissue to elicit a positive control response when tested for complement activation. The tissue prepared by the methods can be utilized and further packaged as a positive control reference material for in-vitro complement assays and diagnostic kits.

In one embodiment, the method comprises providing biological tissue; treating the tissue with an aqueous cellulose solution for a time sufficient to allow fluid in the tissue to be replaced by the aqueous cellulose solution; drying the cellulose-treated tissue by a vacuum-drying or lyophilization process to form dried, cellulose-treated tissue; and storing the dried, cellulose-treated tissue in a dry, ambient environment. In one embodiment, the biological tissue is freshly harvested tissue. In another embodiment, the freshly harvested tissue is further fixed before the cellulose treatment.

The cellulose component, which is non-toxic, includes, but is not limited to, methyl cellulose, ethyl cellulose, hydroxypropyl cellulose and combinations thereof. When fresh biological tissue is treated with an aqueous cellulose solution, the fluid content of the tissue is replaced with cellulose by passive diffusion, and the tissue can be subjected to vacuum-drying or lyophilization. The dried tissue contains collagen and cellulose, and may contain microorganisms possibly contaminated in the biological tissue. Without wishing to be bound by any particular theory, due to its complex composition, the dried tissue prepared by the foregoing method elicits a strong positive control response when tested for in-vitro complement activation.

The present invention also relates to tissue, or an in-vitro complement assay and diagnostic kit containing the same, wherein the tissue is prepared by the processing described above.

DETAILED DESCRIPTION

Figure 1:
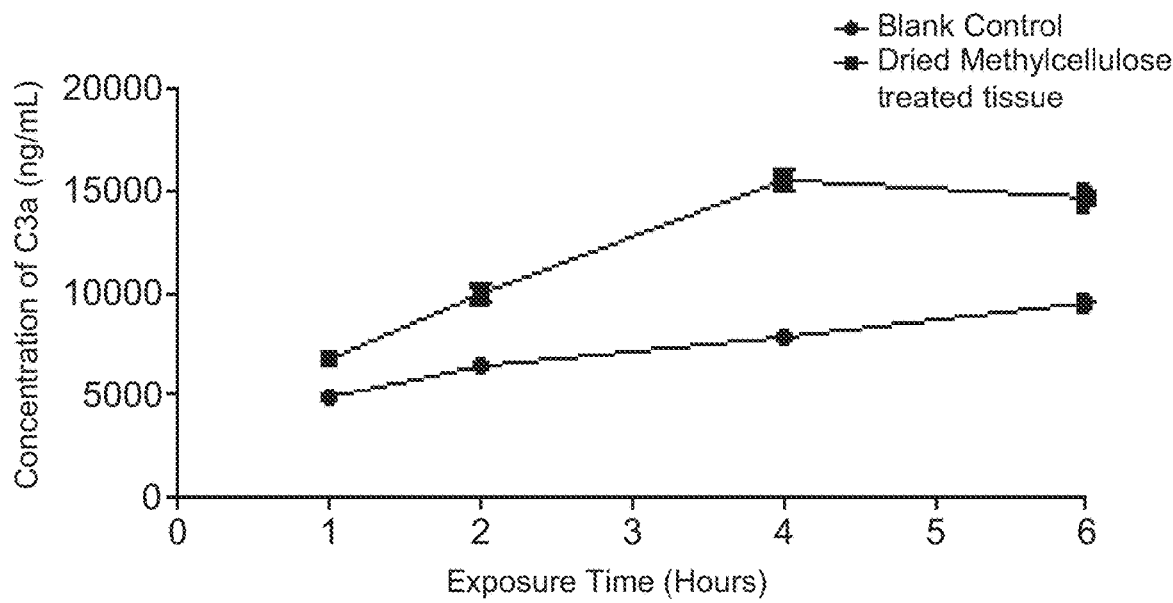
FIG. 1 is a graph showing the concentration of C3a in serum supernatants when the serum was untreated (blank control) and treated with dried, cellulose-treated tissue for different periods of time.

Before describing at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phrasing and terminology employed herein is for the purpose of description and should not be regarded as limiting.

As used herein, the terms "about," "up to," "generally," "substantially" and the like are intended to mean that slight deviations from absolute are included within the scope of the term so modified. A "blank control," used herein, is a serum sample that has not been treated with any material. As used herein, a "fixture," is a structure made of a polypropylene-like material for holding Cuprophan® samples or sheets.

In one aspect, the present invention provides a method of preparing a solid reference material so as to elicit a positive control response when tested for in-vitro complement activation. The solid reference material prepared by the method is dried, cellulose-treated biological tissue. "Biological tissue" or "tissue" as used herein refers to biological tissue dissected from an animal such as, for example, porcine or bovine tissue, or tissue from other animal species. Specific tissue types that may be used include, without limitation, any blood vessel, pericardial tissue, heart muscle tissue, dura mater and the like. "Fresh" biological tissue refers to biological tissue that has been dissected from an animal and not subjected to fixing or cross-linking. "Fixed" or "cross-linked" tissue refers to tissue that has been treated so that the proteins have reduced solubility, antigenicity, and biodegradability as compared to the proteins in the native tissue. "Fixing" or "cross-linking" can be accomplished by a number of techniques, for example, by treatment with aldehydes, epoxides, carbodimides or genipin, or by photo fixation.

In one embodiment, fresh biological tissue is processed directly without being fixed or crossed-linked. In another embodiment, fresh biological tissue is stored in an aqueous storage solution until further processing to prevent drying out and shrinkage of the tissue.

In one embodiment, fresh biological tissue is first fixed or crossed-linked. As noted above, fixing or cross-linking can be accomplished by a number of techniques, for example, by cross-linking with epoxides, carbodimides or genipin, or by photo fixation. Conventionally, fixing can be accomplished by cross-linking the amine groups of the tissue proteins with an aldehyde, such as a solution of about 0.001 v/v %-about 5 v/v % glutaraldehyde or formaldehyde for about several minutes to several weeks. The fixed tissue preferably is rinsed thoroughly with a sterile saline solution to substantially reduce the amount of unreacted fixative within the tissue. Thereafter, the fixed tissue is further processed immediately or stored in an aqueous storage solution until further processing to prevent drying out and shrinkage of the fixed tissue.

In one embodiment, the aqueous storage solution may be sterile saline. A saline solution is generally composed of distilled and/or deionized water and sodium chloride in a concentration ranging from about 0.01 wt % to about 1.5 wt %. More specifically, the sodium chloride concentration can range from about 0.75 wt % to about 1.05 wt %. Isotonic saline is often used. As an alternative to sodium chloride, the following salts may be used for the saline solution: potassium chloride, calcium chloride, magnesium sulfate, disodium phosphate, sodium bicarbonate, magnesium chloride, sodium phosphate, potassium phosphate, or any combination thereof, with or without sodium chloride. Additionally, the saline solution may be a balanced salt solution such as Hank's, Earle's, Gey's or Ouck's balanced salt solution, or may be a phosphate buffered solution.

The fresh or fixed biological tissue (if stored, after removal from the aqueous storage solution) is placed in an aqueous cellulose solution. The cellulose in the solution may include, but is not limited to, methyl cellulose, ethyl cellulose, hydroxypropyl cellulose and combinations thereof. Preferably, the aqueous cellulose solution comprises from about 1 wt % to about 50 wt % of cellulose; more preferably, from about 1 wt % to about 5 wt % of cellulose; and most preferably, about 2 wt % (viscosity 15 cps) of cellulose. The cellulose solution is non-toxic and is currently used in various industries (i.e., cosmetics, food, and medicine). Without wishing to be bound by any particular theory, cellulose is a large polymer that potentially could be trapped in the collagen matrix. Without an enzyme to cleave the linkages, the trapped cellulose will not degrade. The cellulose treatment may help prevent change or damage to the tissue properties during the drying process. The cellulose remaining on the surface of the tissue following treatment with the cellulose solution can be easily removed from the tissue by rinsing or rehydration, such as with a sterile saline solution, including the sterile saline solutions noted above.

The tissue component is contacted with the cellulose solution for a time and at a temperature sufficient to permit the cellulose solution to penetrate into the interstices of the tissue by passive diffusion and replace the fluid therein. The time needed to achieve such replacement is directly related to the thickness of the tissue, and inversely related to the ratio between the volume of the cellulose solution and the volume of the tissue. Biological tissue usually has a thickness of less than 1 mm. Tissue having a thickness of less than 1 mm may be contacted with a cellulose solution at a temperature between about 15° C. and about 30° C. for about one second to about one week; preferably, for at least 8 hours. More preferably, such tissue may be contacted with a cellulose solution at room temperature for about 12 to about 24 hours.

The tissue is contacted with the cellulose solution by a standard method, such as by immersion in the solution. The amount of the cellulose solution should be at least sufficient to fully submerge the tissue. Preferably, the volume of the cellulose solution is at least about 2 times the volume of the tissue that is brought into contact with the solution; more preferably, about 50 times the volume of the tissue; and still more preferably, about 100 times the volume of the tissue.

After soaking in the cellulose solution for a sufficient time, the tissue is removed from the cellulose solution. The cellulose-treated, unfixed tissue is then placed in a jar or other container for vacuum drying or in a lyophilizer for drying by lyophilization. Vacuum drying is a process in which materials are dried in a reduced pressure environment, which lowers the heat needed for rapid drying. As such, vacuum-drying tends to retain the integrity of the original item with less damage. A vacuum is applied to the container having the tissue inside for a time sufficient to remove substantially all the fluid in the tissue, without the application of heat. The vacuum pressure is no more than about 1000 mTorr, preferably no more than about 200 mTorr, and more preferably no more than about 10 mTorr. The tissue can be subjected to vacuum drying for about one minute to about 2 months. Preferably, a vacuum of about 5 mTorr is applied to the container for at least 4 hours. More preferably, a vacuum of about 5 mTorr is applied to the container for about 6 to about 24 hours.

In some instances, the tissue resulting from the cellulose solution treatment is dried by freeze drying, also called lyophilization. Lyophilization techniques generally involve freezing the tissue, followed by drying the frozen tissue by a sublimation process. Some representative lyophilization conditions that may be used in methods for making lyophilized tissue for use in a prosthetic heart valve include: 1) freezing the tissue at about −20° C. for at least 12 hours, followed by a single vacuum-drying step at, for example, 150 mTorr at room temperature for 15-20 hours; 2) freezing the tissue at about −70° C. for at least two hours, followed by annealing (subjecting the frozen tissue to an increased temperature, such as about −20° C., for at least one hour), then again reducing the temperature to about −70° C. for at least two more hours, followed by drying at a reduced pressure of about 150 mTorr at room temperature for at least 12 hours; 3) freezing the tissue at about −40° C. for at least two hours, followed by annealing as discussed previously, again reducing the temperature to about −40° C. for at least two more hours, and then two-stage drying—a first stage at about −5° C. and about 160 mTorr for at least two hours, followed by a second stage at room temperature and about 160 mTorr for at least two hours; and 4) freezing the tissue in liquid nitrogen (at about −210° C. to about −196° C.) for at least two hours and up to about two months, followed by annealing as discussed previously. Various combinations of these and other processes may also be used, or one or more of the processes may be used in series.

The dried, cellulose-treated tissue is stored in a dry, ambient environment essentially free of liquid for later processing. An environment, container or package that is "essentially free of liquid" as used herein means an environment in which the presence of water or other liquids is limited to the content of such liquids in the ambient air (as more precisely expressed as the relative humidity), and the content of liquid contained within the treated tissue disposed within the container or package. Preferably, the dried tissue component is placed into a microorganism resistant package.

After the dried, cellulose-treated tissue component has been placed in the inner space of the package, the package is sealed. In one embodiment, the package is made of a gas permeable material such as Tyvek® (E. I. du Pont de Nemours and Company). The sealed package may then be sterilized such as by a gas sterilization process or by exposure to ionizing radiation. An example of a conventional procedure for gas sterilization by exposure to ethylene oxide involves exposure of the package to a mixture of 10 wt % ethylene oxide and 90 wt % hydrochlorofluorocarbon at a chamber pressure of about 8 to 10 psi and a temperature of about 38° C. for about 24 hours, or a temperature of about 54-57° C. for about 130 minutes. To ensure the inner space remains sterile following sterilization, the package is preferably formed from a material that is impenetrable to microorganisms such as bacteria and fungi.

In one embodiment, after vacuum-drying or freezing-drying, the dried, cellulose-treated tissue is cut into pieces, and then stored in a dry, ambient environment as described above. The tissue may be cut into pieces by any cutting tools including, but not limited to, sterilized scissors. It may be cut into pieces of various shapes and sizes. The shapes of the tissue are not limited, and can be any configurations including rectangles, squares, ovals, circles and any other regular or irregular shapes. The sizes of the dried, cellulose-treated tissue are based upon the amounts of serum that will be used for testing. The surface area of the material that is used for exposure is generally specified by ISO 10993-12 (Biological evaluation of medical devices Part 12: Sample preparation and reference materials). Based on the standard defined in ISO 10993-12, for a dried, cellulose-treated tissue that has a thickness of less than about 0.5 mm, the surface area of the dried tissue needed for every ml of the serum tested is about 6 $cm^2$, and for tissue with a thickness between about 0.5 mm and about 1 mm, the surface area of the dried tissue needed for every ml of the serum tested is about 3 $cm^2$. A piece of the dried, cellulose-treated tissue may have a surface area from about 1 $mm^2$ to about 645 $mm^2$.

In one aspect, the present invention provides the dried, cellulose-treated biological tissue prepared by the above-described methods as a solid reference material to elicit a positive control response when testing for in-vitro complement activation.

In another aspect, the present invention provides in-vitro complement assay kits comprising the dried, cellulose-treated biological tissue prepared by the above-described methods as a solid reference material to elicit a positive control response when testing for in-vitro complement activation. The in-vitro complement assay kits may also comprise a complement standard, a complement antibody, a wash solution, a stop solution, a substrate, a conjugate, and an instruction for use thereof.

In one embodiment, the in-vitro complement assay kit is designed for the quantitative measurement of C3a in human plasma and serum. The kit comprises a complement C3a standard and a complement C3a antibody. In another embodiment, the in-vitro complement assay kit is designed for the quantitative measurement of C9 in human plasma and serum. The kit comprises a complement C9 standard and a complement C9 antibody. In a further embodiment, the in-vitro complement assay kit is designed for the quantitative measurement of SC5b-9 in human plasma and serum. The kit comprises a complement SC5b-9 standard and a complement SC5b-9 antibody.

In another aspect, the present invention provides in-vitro diagnostic kits for complement assays comprising the dried, cellulose-treated biological tissue prepared by the above-described methods as a solid reference material to elicit a positive control response when testing for in-vitro complement activation. The in-vitro diagnostic kits may also comprise a complement standard, a complement antibody, a wash solution, a stop solution, a substrate, a conjugate, and an instruction for use thereof.

In another aspect, the present invention provides a method of utilizing the dried, cellulose-treated biological tissue prepared by the above-described methods as a solid reference material to elicit a positive control response when testing for in-vitro complement activation. The method comprises exposing the dried, cellulose-treated biological tissue to serum for a period of time; decanting the serum supernatant to get a control sample; optionally freezing, storing, and thawing the control sample; and conducting an in-vitro complement activation assay of the control sample to elicit a positive control response.

The size of the dried, cellulose-treated tissue is based upon the amount of serum that would be used for testing. Based on the standard specified by ISO 10993-12, for dried tissue that has a thickness of less than about 0.5 mm, the surface area of the dried tissue should be 6 $cm^2$ for each ml of the serum to be tested, and for dried tissue that has a thickness between about 0.5 mm and about 1 mm, the surface area of the dried tissue should be about 3 $cm^2$ for each ml of the serum to be tested.

The exposure time of the dried, cellulose-treated tissue to the serum to be tested is from about one to about six hours, preferably from about two to about four hours, and more preferably about four hours.

The serum supernatant is then decanted from the tissue and processed for complement activation testing. Alternatively, the decanted serum supernatant is frozen until further processing. Prior to use, the frozen serum is thawed on ice.

The in-vitro complement activation assay includes, but is not limited to, the immunoassay for complement activation "split products" such as C4d, Bb, C3a, C4a, C5a, and SC5b-9; immunohistochemical demonstration of adsorbed activated complement components such as C3b, C4b, and C5b-9; and functional depletion of complement activity such as C9, as C9 is consumed in the Membrane Attack Complex (MAC). In one embodiment, the in-vitro complement activation assay is a quantitative measurement of C3a. In another embodiment, the in-vitro complement activation assay is a quantitative measurement of C9. In a further embodiment, the in-vitro complement activation assay is a quantitative measurement of SC5b-9. The in-vitro complement activation assay is conducted by using an in-vitro complement activation assay kit according to the manufacturer's instructions. The assay kit may be used for measurement of C3a, C9 or SC5b-9.

The following examples are for purposes of illustration only and are not intended to limit the scope of the invention as defined in the claims hereinafter.

Example 1 Preparation of Dried, Cellulose-Treated Tissue

One liter of a 2 wt % methyl cellulose solution was prepared by heating 300 ml of water to at least 80° C., and adding 20 g of methyl cellulose powder to the hot water with agitation. The mixture was further agitated until the methyl cellulose particles were thoroughly wetted and evenly dispersed. 700 ml of cold water or ice was then added to lower the temperature of the dispersion. Once the dispersion cooled to a temperature at which the methyl cellulose became water soluble, the powder began to hydrate and the viscosity of the solution increased. The resulting solution was then cooled in a bath at 0-5° C. for about 20 to 40 minutes under continuous agitation. The solution was continually agitated for at least 30 minutes after room temperature was reached. The viscosity of the resulting methyl cellulose solution was about 15 cPs.

A piece of fresh bovine tissue was then placed into a sufficient amount of the 2 wt % methyl cellulose solution prepared above so as to completely cover the tissue. The tissue was kept in the methyl cellulose solution for about 24 hours at room temperature. The tissue was then removed from the methyl cellulose solution, placed into a jar, and dried by applying a vacuum of 200 mTorr to the jar (with lid removed and the tissue inside) for about 24 hours at room temperature. The jar was then removed from the vacuum appliance and covered with its lid.

Example 2 Application of the Dried, Cellulose-Treated Tissue as a Positive Control in Complement Assay Example 2-1 Treatment of Serum Samples with the Dried, Cellulose-Treated Tissue The dried, cellulose-treated tissue prepared in Example 1 above had a thickness of about 0.5-1.0 mm. It was cut into pieces by a pair of scissors, and each of the pieces had a surface area of about 15 cm². A piece of the dried tissue was exposed to each of four 5 mL serum samples (one piece per serum sample) for four different time periods, i.e., 1, 2, 4 and 6 hours, respectively. The four resulting serum supernatants were then decanted from the tissue and frozen immediately afterwards. All four of these serum supernatant samples stayed frozen for twelve hours and then were thawed on ice prior to use.

In addition to the four serum supernatants prepared above, four 5 mL serum samples that were not treated with or exposed to any materials (i.e., untreated samples as blank controls) were decanted at four different time periods, i.e., 1, 2, 4 and 6 hours respectively, and frozen immediately afterwards. These four untreated samples used as blank controls stayed frozen for twelve hours and then were thawed on ice prior to use.

Example 2-2 Complement Activation Assay of the Serum Supernatant Samples

The serum supernatant samples and untreated samples prepared in Example 2-1 above were processed for complement activation assay using Quidel's C3a Plus EIA Kit and Abcam's C9 Human ELISA Kit according to the manufacturer's instructions.

For Quidel's C3a Plus EIA, a murine monoclonal antibody specific for a neo-epitope on human C3a had been precoated onto a 96-well plate provided in the kit. The serum supernatant samples prepared in Example 2-1 above were diluted 1:5,000 in Specimen Diluent (containing a buffered protein base with 0.05% ProClin® 300) provided in the kit and equilibrated to room temperature before use. The assay was performed at room temperature (18-25° C.). 100 µL of each C3a Plus Standard (A, B, C, D, E) provided in the kit was added to duplicate wells. 100 µL of both the C3a Plus Control and C3a Plus High Control provided in the kit was added to duplicate wells. 100 µL of each of the diluted serum supernatant samples was added to the assigned microassay well and was incubated for 60±10 minutes. The monoclonal antibody became bound to C3a in each of the diluted serum supernatant samples. The liquid from each well was removed by a pipette, and each well was washed with about 300 µL of Wash Solution (containing phosphate buffered saline (PBS), 1.0% Tween-20® and 0.035% Proclin® 300) using a wash bottle. The liquid was subsequently removed from each well by a pipette, and the plate was then inverted and the liquid remaining in each well was decanted. The plate was then tapped on absorbent paper towel to completely remove any remaining liquid. This washing step was repeated four times. 100 µL of horseradish peroxidase (HRP)-Conjugated anti-C3 (C3a) was then added to each well and incubated for 60±10 minutes. The horseradish peroxidase (HRP)-Conjugated anti-C3 (C3a) became bound to the immobilized C3a captured previously. The plate was then washed with Wash Solution as described above to remove any unbound conjugate. 100 µL of Chromogen Substrate (containing 3,3',5,5'-tetramethylbenzidine (TMB) and hydrogen peroxide ($H_2O_2$)) was added to each well, and incubated for 15±1 minutes. The bound HRP reacted with the substrate, forming a blue color. After the incubation period, the reaction was stopped chemically by adding 100 µL of Stop Solution (containing 1N (4%) hydrochloric acid) to each well, which resulted in a color change from blue to yellow. The color intensity was measured by a microplate reader at a wavelength of 450 nm. The density of yellow coloration was directly proportional to the concentration of Complement C3a present in each of the diluted serum supernatant samples. Results were calculated from the generated curve using 4-parameter analysis. The concentration of C3a in each serum supernatant sample is shown in FIG. 1.

For Abcam's C9 Human in vitro ELISA, a Complement C9 specific antibody had been precoated onto a 96-well plate provided in the kit and blocked. The serum supernatant samples prepared in Example 2-1 above were diluted 1:20,000 in Diluent M provided in the kit and equilibrated to room temperature before use. The assay was performed at room temperature (18-25° C.). 50 µL of each of the diluted serum supernatant samples was added to the wells. The wells were covered with a sealing tape and incubated for two hours. The Complement C9 specific antibody became bound to C9 in the diluted samples. The plate was manually washed five times with about 200 µL of Wash Buffer provided in the kit to remove any unbound material. The plate was inverted each time, the liquid in each well was decanted, and the plate was then tapped 4-5 times on absorbent paper towel to completely remove the liquid. 50 µL of Biotinylated Complement C9 Detection Antibody was added to each well and incubated for one hour. The Biotinylated Complement C9 Detection Antibody became bound to immobilized C9 captured previously. The plate was then washed with Wash Buffer as described above to remove any unbound material. 50 µL of Streptavidin-Peroxidase Conjugate was added to each well and incubated for 30 minutes. The unbound conjugates were washed away with Wash Buffer as described above. 50 µL of TMB Chromogen Substrate provided in the kit was added to each well and incubated for 15 minutes or until the optimal blue color density was developed. The plate was gently tapped to ensure thorough mixing. 50 µL of Stop Solution provided in the kit was added to each well and the blue color changed to yellow. The absorption was read immediately on a microplate reader at a wavelength of 450 nm. The density of yellow coloration was directly proportional to the amount of Complement C9 present in each of the diluted serum supernatant samples. Results were calculated from the generated curve using 4-parameter analysis. The concentration of C9 in each serum supernatant sample is shown in FIG. 2.

Figure 2:
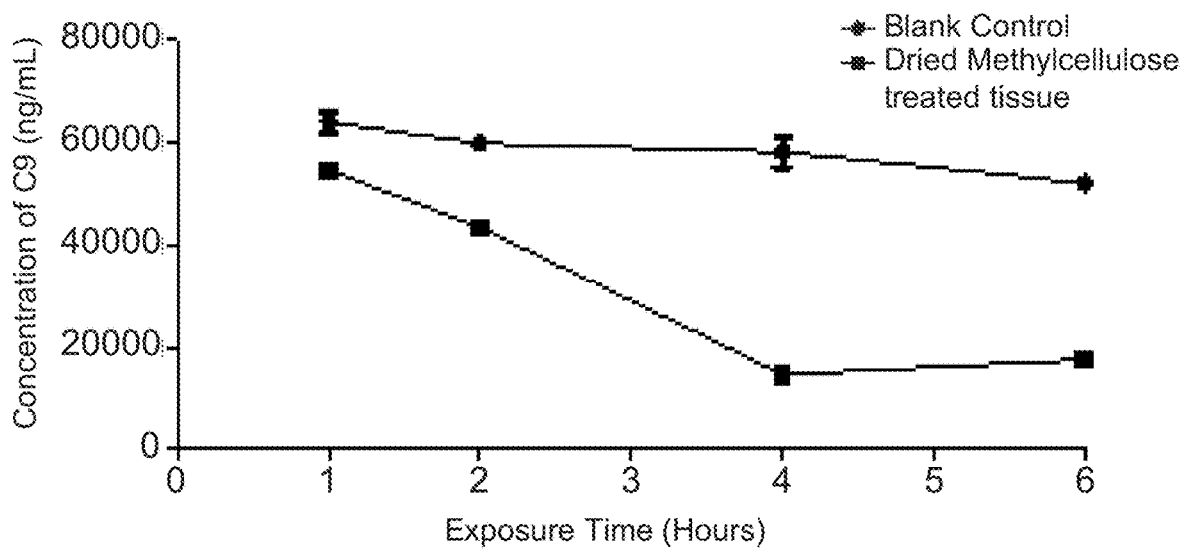
FIG. 2 is a graph showing the concentration of C9 in serum supernatants when the serum was untreated (blank control) and treated with dried, cellulose-treated tissue for different periods of time.

FIG. 1 and FIG. 2 demonstrate the concentrations of C3a and C9, respectively, in the serum supernatants wherein the serum was untreated (blank control) or treated with the dried, cellulose-treated tissue for different periods of time. The figures indicate that the trends in the increase of C3a and in the decrease of C9 are identical for each exposure time point. The exposure of the dried, cellulose-treated tissue to the serum for about one to two hours gave some increase of C3a and some decrease of C9 for the serum supernatants. About four hours of exposure gave the largest increase of C3a and the largest decrease of C9, and about six hours of exposure gave a regression (some decrease in C3a and increase in C9).

Figure 3:
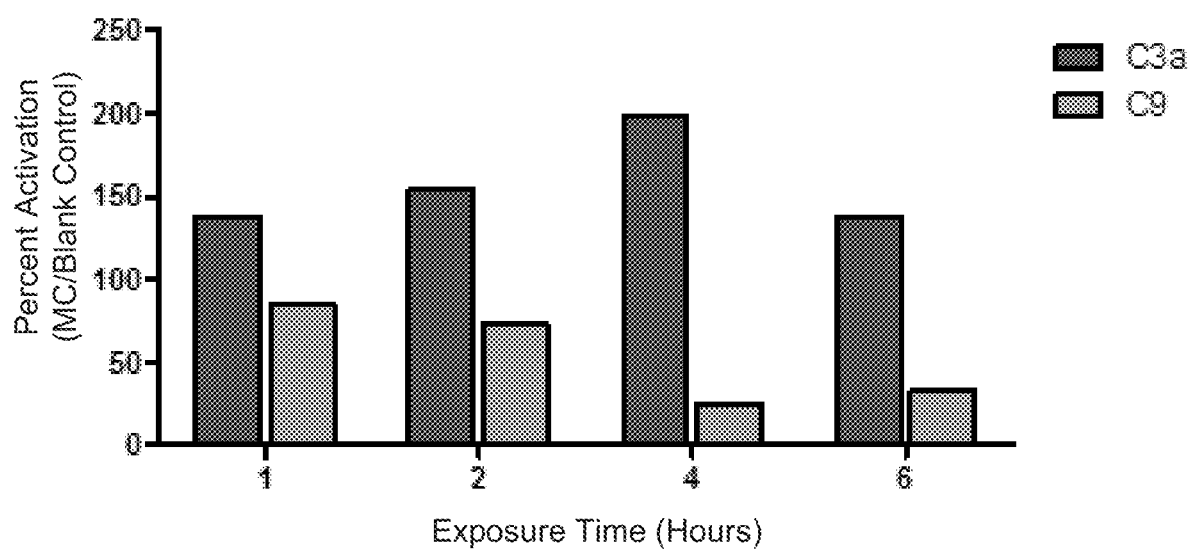
FIG. 3 is a bar graph showing the percentage activation of C3a and C9 over a blank control for serum supernatants when the serum was untreated (blank control) and treated with dried, cellulose-treated tissue for different periods of time.

FIG. 3 demonstrates the percentage activation of C3a and C9 over the blank control for the serum supernatants wherein the serum was untreated (blank control) or treated with the dried, cellulose-treated tissue for different periods of time. The figure shows that exposure of the dried, cellulose-treated tissue to the serum for about four hours yielded a two-fold increase of C3a and a 75% reduction of C9.

These figures demonstrate that the dried, cellulose-treated tissue elicits a strong positive control response when tested for complement activation.

Example 3 Comparison of Different Materials as a Positive Control in Complement Assay Example 3-1 Treatment of Serum Samples with Different Materials 5 mL serum samples were treated with a fixture, a fixture which holds a Cuprophan® sheet, dried tissue (without cellulose treatment), or dried, cellulose-treated tissue for two different time periods, i.e., 1 hour and 4 hours. The Cuprophan® sheet, dried tissue (without cellulose treatment), and dried, cellulose-treated tissue used herein all had a thickness of about 0.5-1.0 mm, and a surface area of about 15 $cm^2$. One 5 mL serum sample not treated with any materials was used as a blank control. The fixture, made of a polypropylene-like material, was a structure for holding Cuprophan® samples or sheets. After the treatment with the fixture, the fixture holding a Cuprophan® sheet, dried tissue (without cellulose treatment), or dried, cellulose-treated tissue, the serum supernatants prepared from these treatments were decanted and frozen immediately afterwards. The serum supernatant samples stayed frozen for twelve hours and then were thawed on ice prior to use.

Example 3-2 Complement Activation Assay of the Serum Supernatant Samples

The serum supernatant samples prepared in Example 3-1 above were processed for complement activation assay using Abcam's C9 Human ELISA Kit and Quidel's SC5b-9 Plus EIA Kit according to the manufacturer's instructions. The detailed procedure using the C9 Human ELISA kit was the same as described above in Example 2-2. The measured concentration of C9 in each serum supernatant sample is shown in FIG. 4.

Figure 4:
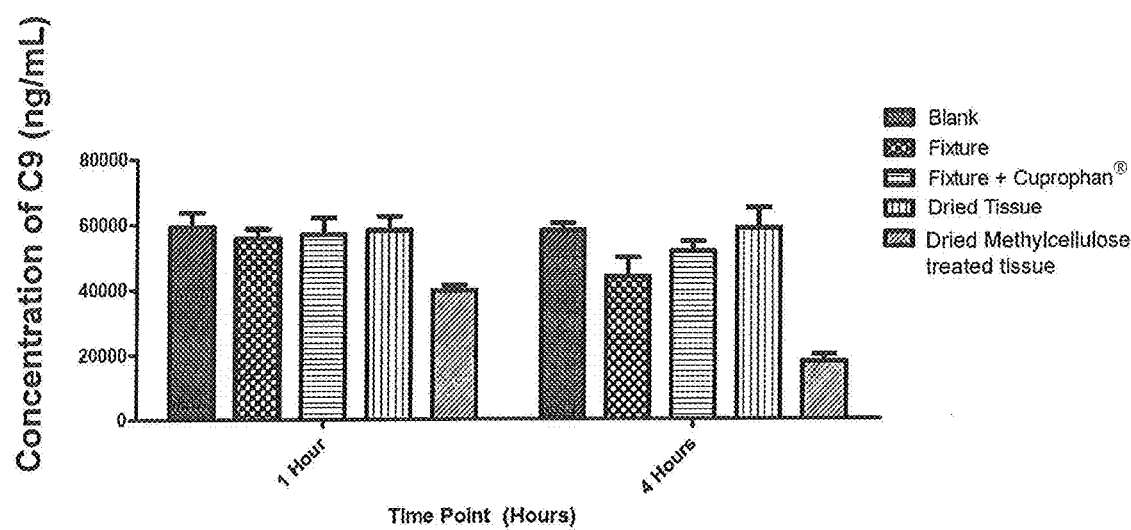
FIG. 4 is a bar graph showing the concentration of C9 in serum supernatants when the serum was untreated (blank control) and treated with a fixture, a fixture holding Cuprophan®, dried tissue (without cellulose treatment), and dried, cellulose-treated tissue for different periods of time. The fixture, made of a polypropylene-like material, is a structure for holding Cuprophan® samples or sheets.

FIG. 4 shows the concentrations of C9 in the serum supernatants wherein the serum was untreated (blank control) or treated with a fixture, a fixture holding a Cuprophan® sheet, dried tissue (without cellulose treatment), or dried, cellulose-treated tissue for two different time periods, i.e., 1 and 4 hours. The figure demonstrates that the dried, cellulose-treated tissue elicits a stronger positive control response when tested for complement activation compared to other materials, such as a Cuprophan® sheet and dried tissue (without cellulose treatment).

For Quidel's SC5b-9 Plus EIA, a mouse monoclonal antibody specific for the C9 ring of SC5b-9 had been precoated onto a 96-well plate provided in the kit. The serum supernatant samples prepared in Example 3-1 above were diluted 1:160 in Specimen Diluent provided in the kit. The microassy wells were first rehydrated by adding approximately 300 μL of Wash Solution provided in the kit using a wash bottle, and incubated at 15° C. to 30° C. for two minutes. The liquid in each well was removed by a pipette. The plate was then inverted and tapped on absorbent paper twice to remove any remaining liquid. 100 μL of each SC5b-9 Standard (A, B, C, D, E) provided in the kit was added to duplicate wells. 100 μL of both the SC5b-9 High Control and SC5b-9 Low Control provided in the kit were added to duplicate wells. 100 μL of each diluted serum supernatant sample was added to the assigned well, and incubated at 15° C. to 30° C. for 60±1 minutes. The monoclonal antibody bound to SC5b-9 in each of the diluted samples. The liquid from each well was removed by a pipette, and the wells were washed with about 300 μL of Wash Solution using a wash bottle. The liquid from each well was removed by a pipette, and the plate was then inverted and the liquid remaining in each well was decanted. The plate was then tapped on absorbent paper towel to completely remove any remaining liquid. This washing step was repeated four times. 50 μL of SC5b-9 Plus Conjugate provided in the kit was added into each washed well, and incubated at 15° C. to 30° C. for 30±1 minutes. The SC5b-9 Plus Conjugate became bound to the immobilized SC5b-9 captured previously. The plate was then washed with Wash Solution as described above to remove any unbound conjugate. 100 μL of TMB Chromogen Substrate provided in the kit was added to each well, and incubated at 15° C. to 30° C. for 15±1 minutes or until the optimal blue color density was developed. After the incubation period, the reaction was stopped chemically by adding 100 μL of Stop Solution provided in the kit to each well, which resulted in a color change from blue to yellow. The color intensity was measured by a microplate reader at a wavelength of 450 nm. The density of yellow coloration was directly proportional to the concentration of Complement SC5b-9 present in each of the diluted serum supernatant samples. Results were calculated from the generated curve using 4-parameter analysis. The concentration of SC5b-9 in each serum supernatant sample is shown in FIG. 5.

Figure 5:
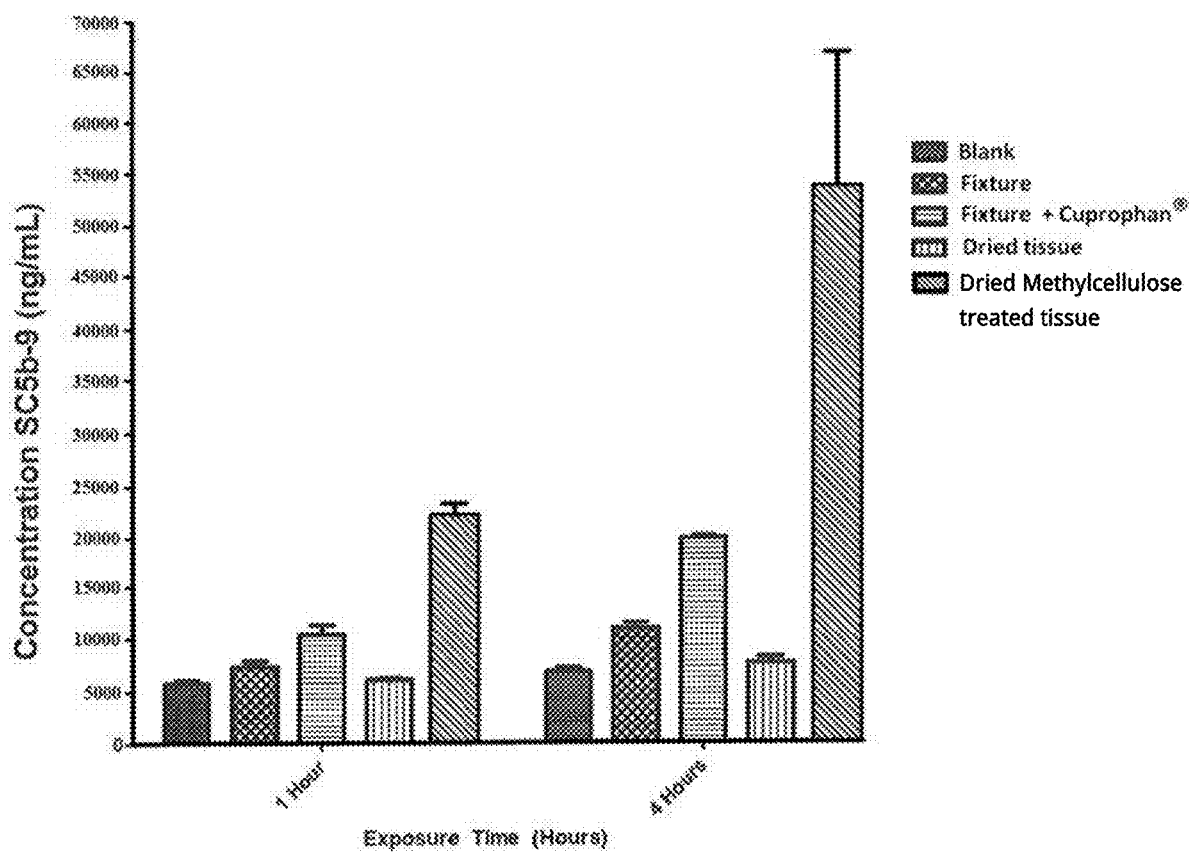
FIG. 5 is a bar graph showing the concentration of SC5b-9 in serum supernatants when the serum was untreated (blank control), treated with a fixture, or treated with a fixture holding Cuprophan®, dried tissue (without cellulose treatment), or dried, cellulose-treated tissue for different periods of time.

FIG. 5 shows the concentrations of SC5b-9 in the serum supernatants wherein the serum was untreated (blank control), treated with a fixture, or treated with a fixture holding a Cuprophan® sheet, dried tissue (without cellulose treatment), or dried, cellulose-treated tissue for two different time periods, i.e., 1 and 4 hours. The figure demonstrates that dried, cellulose-treated tissue elicits a much stronger positive control response when tested for complement activation compared to the Cuprophan® sheet.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a solid in-vitro complement activation assay reference material so as to elicit a positive control response when tested for in-vitro complement activation, comprising:
   providing biological tissue;
   treating the tissue with an aqueous cellulose solution for a time sufficient to allow fluid in the tissue to be replaced by the aqueous cellulose solution, wherein the aqueous cellulose solution comprises between about 1% and about 5% by weight of cellulose selected from the group consisting of methyl cellulose, ethyl cellulose, hydroxypropyl cellulose and combinations thereof;
   drying the cellulose-treated tissue by a vacuum-drying process or a lyophilization process to form dried, cellulose-treated tissue; and
   storing the dried, cellulose-treated tissue in a dry, ambient environment, thereby providing said solid in-vitro complement activation assay reference material.

2. The method of claim 1, wherein the biological tissue is freshly harvested.

3. The method of claim 1, wherein the biological tissue is fixed.

4. The method of claim 1, wherein the cellulose is methyl cellulose.

5. The method of claim 1, wherein the cellulose is included in an amount of about 2% by weight of the aqueous cellulose solution.

6. The method of claim 1, wherein the aqueous cellulose solution has a volume sufficient to fully submerge the tissue.

7. The method of claim 1, wherein the treating step is performed for about one second to about one week.

8. The method of claim 1, wherein the treating step is performed for at least 8 hours.

9. The method of claim 1, wherein the treating step is performed at a temperature between about 15° C. and about 30° C.

10. The method of claim 1, wherein the vacuum-drying process uses a vacuum pressure of no more than 1000 mTorr.

11. The method of claim 1, wherein the vacuum-drying process uses a vacuum pressure of no more than 200 mTorr.

12. The method of claim 1, wherein the drying step is performed at a vacuum pressure of about 5 mTorr for at least 4 hours.

13. The method of claim 1, further comprising cutting the dried, cellulose-treated tissue into pieces.

14. The method of claim 13, further comprising placing the dried, cellulose-treated tissue that is cut in pieces in a package and sealing the package.

15. The method of claim 1, further comprising placing the dried, cellulose-treated tissue in a package and sealing the package.

16. The method of claim 15, further comprising sterilizing the package after the sealing step.

17. A method of using a solid reference material to elicit a positive control response when tested for in-vitro complement activation, comprising:
   exposing the solid in-vitro complement activation assay reference material, prepared according to the method of claim 1 to serum for a period of time to produce a serum supernatant;
   decanting the serum supernatant to get a control sample; and
   conducting an in-vitro complement activation assay of the control sample to elicit a positive control response.

18. The method of claim 17, further comprising freezing, storing, and thawing the control sample before the conducting step.

* * * * *